United States Patent [19]

Bonomo et al.

[11] Patent Number: 4,798,205

[45] Date of Patent: Jan. 17, 1989

[54] METHOD OF USING A SUBPERIOSTEAL TISSUE EXPANDER

[75] Inventors: Donald J. Bonomo, Olympia Field, Ill.; Robert C. Paulson, Goleta, Calif.

[73] Assignee: Cox-Uphoff International, Carpinteria, Calif.

[21] Appl. No.: 113,228

[22] Filed: Oct. 23, 1987

Related U.S. Application Data

[62] Division of Ser. No. 861,059, May 8, 1986, Pat. No. 4,719,918.

[51] Int. Cl.$^4$ ............................................. A61M 29/02
[52] U.S. Cl. ................................. 128/344; 128/897; 433/173
[58] Field of Search ............... 128/344, 1 R; 433/36, 433/215, 173

[56] References Cited

U.S. PATENT DOCUMENTS

| | | | |
|---|---|---|---|
| 1,235,095 | 7/1917 | Beck | 128/344 X |
| 4,095,295 | 6/1978 | Lake | 623/8 |
| 4,190,040 | 2/1980 | Schulte | 128/1 R |
| 4,217,889 | 8/1980 | Radovan et al. | 128/1 R |
| 4,338,941 | 7/1982 | Payton | 128/344 X |

OTHER PUBLICATIONS

Cox-Uphoff International Brochure, Aug. 1985 (Doc. 10083-8508).
Cox-Uphoff Product Data Sheet, Sep. 1985 (Doc. 120060-8509).

Primary Examiner—Michael H. Thaler
Attorney, Agent, or Firm—Knobbe, Martens, Olson & Bear

[57] ABSTRACT

Disclosed is a subperiosteal tissue expander for reconstruction of the edentulous atrophied alveolar ridge of the mandible or maxilla. The expander includes an inflatable tube curved into a "C" shape to match the curvature of the human alveolar ridge, having a layer of reinforcement material on one side of the inflatable tube and tabs for attachment of lines at either end of the inflatable tube. Also disclosed is a method for reconstructing the edentulous atrophied alveolar ridge of the maxilla or the mandible by placing a tissue expander subperiosteally along the alveolar ridge of the maxilla or mandible, inflating the expander to create a subperiosteal channel, removing the expander, and filling the subperiosteal channel with a hard material such as hydroxylapatite.

8 Claims, 1 Drawing Sheet

U.S. Patent  Jan. 17, 1989  4,798,205
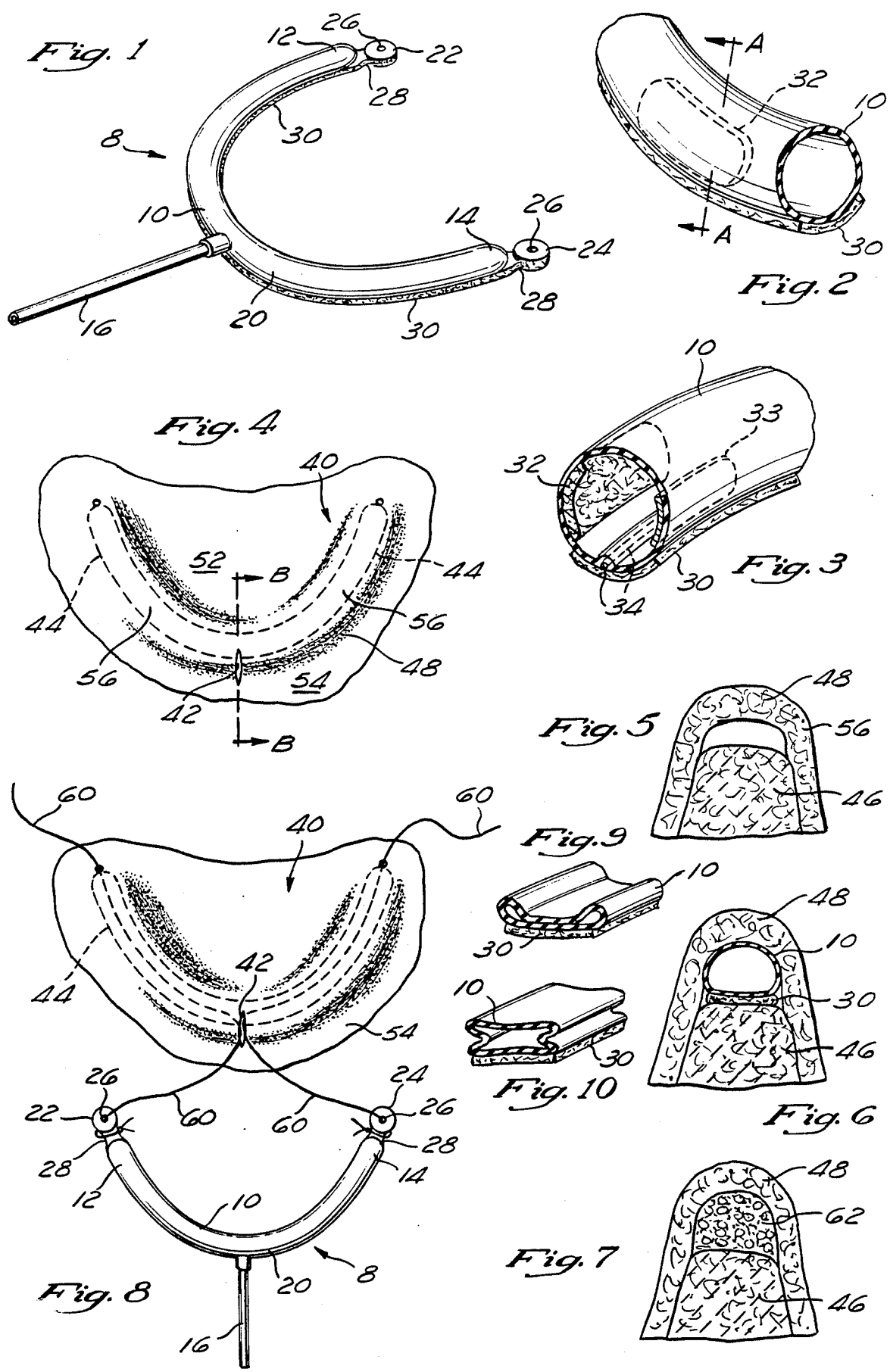

METHOD OF USING A SUBPERIOSTEAL TISSUE EXPANDER

This application is a continuation of application Ser. No. 861,059, filed May 8, 1986. now U.S. Pat. No. 4,719,918

This invention relates to a method and device for reconstruction of the atrophied alveolar ridge, and more particularly, it relates to a subperiosteal tissue expander and a method for using the same.

BACKGROUND OF THE INVENTION

The human jaw bone, or mandible, and the upper jaw, or maxilla, undergo significant changes with age. When teeth are lost, the alveolar process is gradually resorbed presumably because of the loss of ossification-stimulating pressure from the teeth. As the resorption process advances, the size of the bone is dramatically altered. For this reason, a number of surgical procedures have been developed to reconstruct the alveolar ridge of the mandible or maxilla.

Although these reconstruction procedures have been practiced successfully, they are not without problems. Some procedures involve opening the mucoperiosteum along the entire length of the atrophied alveolar ridge, and then attempting to place the hydroxylapatite along the top of the edentulous atrophied alveolar ridge and maintain the hydroxylapatite in place while suturing the delicate mucoperiosteum (not stretched) back together. Tearing of the mucoperiosteum and shifting of the hydroxylapatite, as well as insufficient reconstruction, are significant problems with this technique.

Yet another technique involves creating an envelope or channel running from a midline incision through the mucoperiosteum back along the alveolar ridge. It is difficult, with this technique, to accurately place the hydroxylapatite, and the surgeon is often unable to achieve the desired reconstruction of the atrophied ridge without perforation or stretching of the mucoperiosteum to the point that pressure necrosis develops.

Conventional surgical techniques often present difficulties in maintaining the hydroxylapatite particles along the alveolar ridge without migration of the particles into the lingual sulcus or the buccal and labial vestibules. Sometimes, in attempting to obtain adequate tissue coverage, the buccal vestibule is obliterated, necessitating a later vestibuloplasty. Lip parasthesia from damage to the mental nerves can also result. Stents are commonly used for the control of the particles, which can cause erosion of the mucosa and dehiscence of the hydroxylapatite from stent pressure.

The present invention avoids many of the foregoing problems and permits a more simplified and effective means for reconstruction of the atrophied alveolar ridge.

SUMMARY OF THE INVENTION

In accordance with the present invention, an expandable or inflatable device is placed subperiosteally on the edentulous maxillary or mandibular ridge. Expansion of this device, usually gradual expansion over a period of several days or weeks, forms a well-defined channel or envelope along the edentulous alveolar ridge and under the periosteum. This envelope or channel contains and controls the hydroxylapatite introduced thereinto and the dangers associated with other techniques of necrosis, tissue sloughing, mental nerve parasthesia, migration of hydroxylapatite, obliteration of the buccal vestibule, mucosal erosion, dehiscence, hematoma formation, infection, and difficulties in proper placement of the hydroxylapatite are minimized or eliminated.

Thus, the present invention includes a subperiosteal tissue expander, comprising an elongated inflatable tube, preferably of elastomeric material, having a first end and a second end, the tube preferably being longitudinally curved into at least a segment of a "C" shape, means for filling the tube with a fluid, and means for sealing the fluid inside the tube. The tubes is sized to fit the alveolar ridge of a human in a subperiosteal application. The means for filling the tube can comprise a valve, as disclosed in U.S. Pat. No. 4,178,643, or it may be a cannula on the tube in fluid connection with the interior of the tube. The means for filling the tube may also comprise a self-sealing elastomeric material on the tube through which a filling needle may be inserted, wherein the puncture hole made by the needle is sealed against fluid leakage by the self-sealing material when the needle is withdrawn. Suitable self-sealing materials include an elastomeric material bonded to the inside wall of the expander, such as polybutadiene, silicone rubber, or polyphosphazene.

The means for filling the tissue expander is preferably medially located between the ends of the tube.

In accordance with a preferred embodiment of the present invention, thickened or reinforced tabs are provided at one or both ends of the tube to provide for attachment of sutures and the like. The tab preferably has a hole therethrough for attachment of a suture or a line.

In yet another embodiment of the present invention, the tube further includes a reinforced layer on one side of the tube running from one end of the tube to the other. This reinforcing layer may comprise a thickened portion of the tube or it may be a separate material bonded to the tube, such as a fabric-reinforced silicone sheet. The tab may be an extension of the reinforcing layer.

In still another embodiment of the present invention, the tube further includes a radiopaque material.

In one embodiment of the invention, the deflated tube has a crescent-shaped or pleated cross-section.

The preferred elastomeric material for the tube is cross-linked silicone polymer.

The present invention also encompasses a method for reconstructing the alveolar ridge of the mandible or maxilla. This method includes the steps of making an incision in the mucoperiosteum on the alveolar ridge, creating a subperiosteal channel or envelope leading from the incision along the alveolar ridge, introducing the expandable tube into the channel, and expanding the tube. The incision used is preferably a midline incision, and the channel a bilateral channel directed posteriorly from the incision toward the retromolar pads.

In accordance with a preferred embodiment, the method for reconstructing the alveolar ridge of the mandible or maxilla utilizes an expandable tube with a tab at at least one end thereof. The tab is suitable for attachment of a suture, and the method further comprises the steps of introducing a line (such as a suture) through the nucoperiosteum into the channel at a point removed from the incision and passing the line through the channel and out of the incision, attaching the line to the tab on the tube, and pulling the tube into the channel with the line. The channel preferably runs from a first end on one side of the incision to a second end on the other side of the incision, along the alveolar ridge, and the expandable tube preferably has a first tab and a second tab at opposite ends thereof, and the tabs are adapted for attachment of lines thereto. In accordance with this embodiment, the method further comprises the steps of placing a first line through the mucoperiosteum into the first end of the channel, through the channel to the midline incision, and out of the midline incision, placing a second line into the second end of the channel in the same way, attaching the first line to the first tab and the second line to the second tab, and pulling the tube into the channel with the first line and the second line.

In the surgical method, the procedure may further include the steps of continuing to expand the tube over a period of at least four days and leaving the tube in the channel until the mucoperiosteum has been stretched or hypertrophied so that an enlarged channel remains after removal of the tube. Once the tube has been removed from the enlarged channel, the channel is filled with a hard material. Suitable hard materials include transplanted bone, polylactic acid, and hydroxylapatite. Hydroxylapatite in granular form is preferred.

Many other aspects of the present invention will become apparent from the drawings and the detailed description which follows.

BRIEF DESCRIPTION OF THE DRAWINGS

FIG. 1 is a perspective view of the subperiosteal tissue expander of the present invention.

FIG. 2 is a fragmentary view of a portion of the subperiosteal tissue expander, showing the placement of self-sealing material through which a needle may be introduced to fill the tissue expander with fluid.

FIG. 3 is a sectional view of the tissue expander taken along the line A—A in FIG. 2 and showing the location of the self-sealing material and the reinforcing layer on the inflatable tube.

FIG. 4 is a perspective view of the alveolar ridge of a patient and illustrates the placement of the subperiosteal tissue expander.

FIG. 5 is a sectional view of the mandible of a patient, taken along the line B—B in FIG. 4.

FIG. 6 is a sectional view of the mandible of a patient taken along the line B—B in FIG. 4, and illustrating the placement of the tissue expander in a subperiosteal channel.

FIG. 7 is a sectional view of the mandible of a patient taken along the line B—B in FIG. 4, illustrating the placement of hydroxylapatite or other suitable material in the subperiosteal channel following the removal of the tissue expander.

FIG. 8 corresponds to FIG. 4 and illustrates the method for pulling the tissue expander into the subperiosteal channel.

FIG. 9 is a sectional view of one deflated embodiment of the tissue expander.

FIG. 10 is a sectional view of another deflated embodiment of the tissue expander.

DETAILED DESCRIPTION OF PREFERRED EMBODIMENTS

With reference to FIG. 1, the subperiosteal tissue expander 8 of the present invention comprises an elongated inflatable tube 10 having a first end 12 and a second end 14. The inflatable tube 10 is preferably curved into a "C" shape to match the curvature of the human alveolar ridge. (For partial ridge reconstruction, a smaller expander 8 that is curved into only a segment of a "C" shape is used). The subperiosteal tissue expander 8 is sized to fit subperiosteally along the alveolar ridge of a human, preferably an adult human.

The inflatable tube 10 may be made of any suitable leak-proof material, such as polymer-coated fabric, rubber or any of the synthetic plastics. However, the inflatable tube 10 is preferably made of an elastomeric material such as polybutadiene, processed collagen, natural or synthetic latex rubber, polyphosphazene, or a silicone. The preferred material is a silicone rubber, such as an alkylated polysiloxane, and the preferred silicone rubber is a crosslinked polydimethyl siloxane. Because the subperiosteal tissue expander 8 is intended for implantation in the human body, the bioreactivity of the material on the exterior of the subperiosteal tissue expander 8 is of concern. Polydimethyl siloxane exhibits excellent biocompatibility properties.

Means are provided on the subperiosteal tissue expander 8 for filling the inflatable tube 10 with a fluid. In FIG. 1, the filling means comprises a cannula 16. (The term "cannula" is used herein to refer to a small tube.) Although the cannula 16 may be located at any point on the inflatable tube 10, such as at the first end 12 or the second end 14, it is preferably medially located on the inflatable tube 10 between the first end 12 and the second end 14. The cannula 16 is in fluid connection with the inside of the inflatable tube 10 to permit filling of the inflatable tube 10 with a fluid, specifically a liquid, such as saline, or a gas, such as air. The cannular 16 is preferably located on the outside curvature 20 of the subperiosteal tissue expander 8, which is the labial or buccal side of the subperiosteal tissue expander 8. The cannula 16 may be made of any suitable material, and is preferably made from an alkylated polysiloxane. It may advantageously be made of the same material as the inflatable tube 10.

At least one end of the subperiosteal tissue expander 8 is provided with a tab for attachment of a line (such as a suture). In a preferred embodiment, a first tab 22 is provided at the first end 12 of the inflatable tube 10 and a second tab 24 is provided at the second end 14 of the inflatable tube 10. The first tab 22 and the second tab 24 are made of reinforced material in that they are strong enough to withstand the attachment of a line and the forces generated in pulling the subperiosteal tissue expander 8 by the tab through a subperiosteal channel. The tabs 22, 24 may be made of the same material as the inflatable tube 10, or they may be made of another suitable material, such as a cloth-reinforced polymer. Suitable polymers for the tabs 22, 24 include silicone, polyvinylchloride, polytetrafluoroethylene, and the like. Alternatively, the tabs 22, 24 may be made of cloth, such as polyester or nylon, or metal, such as stainless steel. It is preferred that the tabs 22, 24 include means for attachment of a line, such as a suture. The attachment means may comprise a hole 26 through the tab, a recess 28 on the side of the tab, or any other conventional structure such as a loop or a hook.

Because the inflatable tube 10 may be somewhat delicate and susceptible to rupture or damage during subperiosteal placement, a reinforcing layer 30 is provided on the outside of the inflatable tube 10 on the side thereof that is likely to be in contact with the alveolar ridge when the subperiosteal tissue expander 8 is implanted. Thus, the reinforcing layer preferably runs generally longitudinally on one side of the inflatable tube 10 from the first end 12 to the second end 14 of the inflatable tube 10. The side of the inflatable tube 10 to which the reinforcing layer 30 is attached, or on which the reinforcing layer is provided, is hereinafter referred to as the bottom side of the subperiosteal tissue expander 8 and the inflatable tube 10. In one embodiment of the present invention, the reinforcing layer 30 may extend beyond the first end 12 and the second end 14 of the inflatable tube 10 to form the tabs 22, 24.

The reinforcing layer 30, in a simple embodiment, may comprise a thickened portion on the bottom side of the inflatable tube 10. In a preferred embodiment, the reinforcing layer 30 is a separate sheet of material that is bonded to the bottom side of inflatable tube 10. This separate sheet of material may comprise a fabric or a fabric-reinforced polymer, or simply a solid polymer sheet. A preferred fabric is polyester, particularly the polyester made by DuPont Company under the trademark "DACRON". The location of the reinforcing layer 30 on the inflatable tube 10 is shown in a cross-section of the subperiosteal tissue expander 8 in FIG. 3.

As an alternative to the filling cannula 16, the means for filling the inflatable tube 10 with a fluid may comprise a self-sealing material 32, as shown in FIGS. 2 and 3. The self-sealing material 32 is preferably an elastomeric material through which a filling needle may be inserted, which has the property of sealing the puncture hole caused by the filling needle against fluid leakage upon withdrawal of the needle. Suitable self-sealing elastomeric materials include polybutadiene, silicone, polyvinylchloride, and polyphosphazene as well as numerous other materials that are well known in the art. The self-sealing material 32 is preferably in the form of a sheet or path bonded to the inflatable tube 10. Although the self-sealing material 32 may be bonded to the outside of the inflatable tube 10, in a preferred embodiment, the self-sealing material 32 is located on the inside of the tube 10, but can be located on the outside. The self-sealing material 32 may be located generally lingually on the inflatable tube 10 between the first end 12 and the second end 14, or it may be located at any other point on the inflatable tube 10. However, the self-sealing material 32 is preferably located on the upper side or the labial side of the inflatable tube 10.

Because a needle extended too far through the self-sealing material 32 could pierce the inflatable tube 10 on the opposite side of the tissue expander 8, a puncture guard 33 (shown in phantom in FIG. 3) to prevent leakage may be situated on the inflatable tube opposite the self-sealing material 32. This puncture guard 33 may be metal or other hard material to stop the needle and prevent puncture of the tube 10, or it may be self-sealing material, preferably of the same type as the self-sealing material 32, to simply prevent leakage if inadvertent puncture of the tube occurs.

The expandable envelope 10 may advantageously be manufactured through use of a solution-casting technique. In solution casting, a mandrel of the desired shape is repeatedly dipped in a dispersion of polymer and solvent to build up the desired thickness of polymer on the outside of the mandrel. Thus, to make the inflatable tube 10, a mandrel that is unaffected by the solvent and that has the shape of the desired tube may be repeatedly dipped into a suitable polymer dispersion, such as a polydimethyl siloxane gum filled with reinforcing filler, crosslinker, and catalyst, and a suitable organic solvent such as 1,1,1-trichloroethane or xylene. A suitable polymer dispersion is marketed by Dow-Corning Company under the trade designation "SILASTIC Q7-2213". The organic solvent is allowed to evaporate between mandrel dippings. When the desired envelope or tube thickness is obtained, the mandrel is placed in an oven that is warmed to about 250° F. The heat from the oven initiates the crosslinking reaction that converts the filled gum into an elastomer. Once this crosslinking or curing process has been completed, the inflatable tube 10 is removed from the mandrel (usually by making a slit or hole in the tube 10 that is later repaired) and the mandrel is used to make another inflatable tube.

When the filling means for the subperiosteal tissue expander 8 is the self-sealing material 32, a sheet of self-sealing material 32 in the desired size is attached to the appropriate spot on the mandrel prior to coating the mandrel with elastomer. The elastomer bonds to the self-sealing material 32 when the mandrel is coated during the solution casting process.

The cannula 16 may be bonded to the inflatable tube 10 or it may be cast as part of the inflatable tube 10 so that the inflatable tube 10 and the cannula 16 comprises a single piece with no joints.

The reinforcing layer 30 may be attached to the inflatable tube 10 either before or after the crosslinking process. Any conventional attachment method, such as primary bonding or secondary bonding may be used. Suitable adhesives include silicone adhesives, such as Dow Corning Mecial Adhesive type A.

The tabs 22, 24 may also be molded as part of the inflatable tube 10 or, in a preferred embodiment, they are bonded to the reinforcing layer 30. In one preferred embodiment, the tabs 22, 24 simply constitute an extension of the reinforcing layer 30 out beyond the ends 12, 14 of the inflatable tube 10. Because of the pulling force that may be applied to the tabs 22, 24, they are usually made significantly thicker than the rest of the reinforcing layer 30 to lessen the chance of the suture or line tearing them.

In order to permit easy radiographic visualization of the expander 8, a suitable radiopaque material 34 may be placed in the expander 8, as shown in FIG. 3. The radiopaque material may be a wire of any suitable metal, or it may constitute a suitable radiopaque salt molded into the tube 10, the reinforcing layer 30, or the tabs 22, 24. Any of the various well-known radiopaque materials can be used. Suitable materials include tantalum oxide and barium sulfate. In a preferred embodiment, the radiopaque material 34 comprises a wire (as shown in FIG. 3) running the length of the expander 8. This wire may advantageously be situated between the tube 10 and the reinforcing layer 30.

It is important that the expander 8 lie flat when deflated. A flat profile facilitates subperiosteal insertion of the expander 8. Thus, the expander 8 is preferably molded to exhibit a relatively shallow profile when deflated. As shown in FIG. 9, the shape of the expander 8 (and particularly of the tube 10) in cross-section may be a crescent shape. Alternatively, as shown in FIG. 10, a pleated configuration may be provided in order to facilitate collapse of the deflated expander 8.

The surgical method for reconstruction of the alveolar ridge of the mandible or maxilla is illustrated in FIGS. 4–8. With reference to FIG. 4, in order to permit subperiosteal placement of the tissue expander 8 along the alveolar ridge 40, an incision 42 is made through the mucoperiosteum. Although location of the incision 42 is, to some degree, discretionary, it is preferred that the incision be approximately a one centimeter midline incision just below the alveolar ridge of the edentulous mandible. A periosteal elevator is introduced through the incision 42 and is directed posteriorly to the retromolar pad. Care should be taken to remain in contact with the bone 46 at all times. (See FIG. 5.) The periosteum 48 is stripped along the alveolar ridge toward the lingual side 52, keeping the periosteum on the buccal side 54 intact to prevent obliteration of the buccal vestibule. Elevation of the periosteum 48 should be kept to a minimum, and only a small channel, five to seven millimeters in width, is sufficient for placement of the tissue expander 8. The channel 56 is shown in phantom in FIG. 4, and leads from the incision 42 along the alveolar ridge of the mandible bone 46. The channel 56 is preferably a bilateral channel directed posteriorly from the incision 42 toward the tetromolar pad 44.

A line 60 is then introduced through the mucoperiosteum 48 and into the channel 56. (See FIG. 8.) The line 60 then passes through the channel 56 and out of the incision 42, and is attached to an end 12, 14 of the tissue expander 8. In a preferred embodiment, two lines 60 are used, each line running from a different end of the channel 56, through the channel 56, and out of the incision 42. Each line is then attached to an opposite end of the tissue expander 8, and preferably to the tabs 22, 24. The line 60 is preferably a suture, and the line 60 may be introduced into the channel 56 by means of an awl.

Once the lines 60 have been attached to the ends 12, 14 of the tissue expander 8, the tissue expander 8 is drawn into the channel 56 by means of the line or lines 60. The tissue expander 8 may be secured in place by suturing the line 60 to the retromolar pad area 44. After closing the incision 42, the tissue expander 8 is then filled with a fluid, preferably saline, until the tissues are elevated without compromise to the blood supply. FIG. 6 illustrates the inflated expander in place. Care is taken not to overinflate the tissue expander 8, as this may cause restriction of the blood supply. Where the tissue expander 8 is provided with a cannula 16 for filling the tissue expander, the cannula 16 preferably extends out through the incision 42. After filling the tissue expander to the appropriate height, which initially requires about 1 to 3 cc saline (depending on the size of the expander), the cannula 16 is clamped with a hemostat and is then cut to the desired length. Doubling the cannula and tying it with a silk suture will prevent leakage of filling fluid through the cannula 16. Alternatively, the cannula 16 may be sealed with a plug (not shown) of any suitable material, such as silicone, polypropylene, polybutadiene, or polyphosphazene. The cannula 16 may be sutured to the vestibule to prevent its movement and to prevent irritation until the next inflation.

Periodically over the ensuing seven to fourteen days, the tissue expander 8 is further inflated, until the desired expansion of the mucoperiosteum is achieved. Close monitoring of the tissues is necessary to detect any compromise in blood supply. Filling fluid must be withdrawn from the expander if there is any inhibition of blood supply.

When adequate expansion of the mucoperiosteum has been achieved, the tissue expander 8 is removed from the now enlarged channel 56 and is discarded. A suitable hard, biocompatible material 62, such as autogeneous bone, calcium phosphate, polylactic acid, collagen, or synthetic hydroxylapatite or other ceramic material is then introduced into the channel 56. (See FIG. 7.) Of these materials 62, hydroxylapatite is preferred. The hard material 62 is introduced into the channel 56 through the incision 42 (through which the tissue expander 8 was removed), after which the incision 42 is closed.

The foregoing surgical procedure has been described in terms of the mandible. Of course, the same procedure can also be applied to reconstruction of the maxilla.

Although the present invention has been described and illustrated in the context of certain preferred embodiments, it will be understood that some modifications may be made without departing from the spirit of the invention. Accordingly, it is intended that the scope of the present invention be determined by reference to the claims which follow.

What is claimed is:

1. A method for forming an enlarged subperiosteal channel along the alveolar ridge of the mandible or maxilla, comprising the steps of:
    making an incision in the mucoperiosteum on the alveolar ridge;
    creating a subperiosteal channel leading from said incision along the alveolar ridge;
    introducing an expandable tube into said channel;
    expanding said tube; and
    leaving said tube in said channel until said mucoperiosteum has stretched or grown so that an enlarged channel remains after removal of said tube.

2. The method of claim 1, wherein said incision is a midline incision.

3. The method of claim 2, wherein said channel is a bilateral channel directed posteriorly from said incision toward the retromolar pads.

4. The method of claim 3, wherein said expandable tube has a tab at one end suitable for attachment of a line, said method further comprising the steps of:
    introducing a line through said mucoperiosteum into said channel at a point removed from said incision;
    attaching said line to said tab on said tube; and
    pulling said tube into said channel with said line.

5. The method of claim 1, wherein said channel runs from a first end on one of said incision to a second end on the other side of said incision, and wherein said tube has a first tab and a second tab at opposite ends thereof, said tabs adapted for attachment of lines thereto, wherein said method further comprises the steps of:
    placing a first line through the mucoperiosteum into said first end of said channel, through said channel to said incision, and out of said incision;
    placing a second line through the mucoperiosteum into said second end of said channel, through said channel to said incision, and out of said incision;
    attaching said first line to said first tab and said second line to said second tab; and
    pulling said tube into said channel with said first line and said second line.

6. The method of claim 1, further comprising the steps of:
    removing said tube from said enlarged channel; and
    filling said channel with a hard material.

7. The method of claim 6, wherein said hard material is a ceramic material.

8. The method of claim 6, wherein said hard material is hydroxylapatite.

* * * * *